United States Patent [19]

Matsumoto et al.

[11] Patent Number: 4,492,644
[45] Date of Patent: Jan. 8, 1985

[54] SLOWLY RELEASING PERFUME COMPOSITIONS

[75] Inventors: Yuuichi Matsumoto, Abiko; Kiyomitsu Kawasaki, Noda; Masato Ishitani, Kashiwa, all of Japan

[73] Assignee: Soda Aoromatic Company, Limited, Tokyo, Japan

[21] Appl. No.: 368,520

[22] Filed: Apr. 15, 1982

[51] Int. Cl.$^3$ ............................................. A61K 7/46
[52] U.S. Cl. ............................................. 252/522 A
[58] Field of Search ................................. 252/521 A

[56] References Cited

U.S. PATENT DOCUMENTS 3,994,439 11/1966 Van Breen et al. ............ 252/522 A
4,095,031 6/1978 Engle .............................. 252/522 A

FOREIGN PATENT DOCUMENTS 121560 9/1981 Japan ............................. 252/522 A Primary Examiner—Anton H. Sutto
Attorney, Agent, or Firm—Scully, Scott, Murphy & Presser

[57] ABSTRACT

A slowly releasing perfume composition is obtained by mixing a granulated ethylene-vinyl acetate copolymer and a perfume which contains hydrocarbons and/or esters as an essential fragrant component, at a temperature in the range of about 10° C. to about 50° C.

4 Claims, No Drawings

SLOWLY RELEASING PERFUME COMPOSITIONS

BACKGROUND OF THE INVENTION

The present invention relates to slowly releasing perfume compositions.

As slowly releasing perfume compositions mainly occupying the aromatic market at present there are so-called gel aromatics comprising water-soluble gels such as agar and carrageenan and perfumes dispersed therein using surfactants. Such gel aromatics have a superior volatilization mechanism such that they slowly release the perfumes dispersed therein along with gradual evaporation of water, and they can be colored easily into beautiful colors. Because of these superior characteristics, such gel aromatics are relatively popular. However, such gel aromatics have various drawbacks. For example, they always require a solid container as a protector for covering up the drawback of water-soluble gels that the gels easily get out of shape when a physical external force is exerted thereon; the amount of a perfume which can be dispersed in the gel is at most 10% or so of the weight of the gel, therefore in order to be fully effective during the period of use required of ordinary aromatics, namely, one to two months, it is necessary to use a relatively large amount, 70 to 150 grams, of a gel aromatic for each aromatic commodity; because the gel used is a water-soluble gel, it easily freezes at a temperature below 0° C. and causes a phenomenon of water separation when thawing; and because the gel surface hardens in the form of a film along with evaporation of water, the effective volatilization percentage of the perfume dispersed in the gel is relatively small (35% or so of the dispersed perfume on an average).

There are also known various scented plastics comprising thermoplastic resins and small amounts of perfumes contained therein. Such scented plastics are obtained by adding a perfume beforehand to a starting resin before molding followed by melt-kneading under application of heat at a temperature of about 150° C. to about 200° C. and then molding the mixture by a conventional molding method. In such a method, however, the heating step causes volatilization of a low boiling portion of the perfume and a qualitative thermodeterioration, thus resulting in that the fragrance of the resultant scented molding is in many cases markedly different from that of the perfume used, and in order to prevent such an inconvenience it is inevitably required to restrict the perfume components use to high boiling components difficult to undergo such volatilization and thermal deterioration. Moreover, such scented plastics are not considered to satisfy both intensity and durability of fragrance.

SUMMARY OF THE INVENTION

It is an object of the present invention to provide novel, slowly releasing perfume compositions which permit a uniform volatilization of perfume over a long period of time.

It is another object of the present invention to provide novel, slowly releasing perfume compositions which do not undergo swelling, softening, deformation or the like even if the perfume content thereof is relatively large.

Other objects and advantages of the present invention will become apparent from the following description.

The above objects of the present invention can be attained by mixing a granulated ethylene-vinyl acetate copolymer and a perfume containing as an essential component at least one fragrant component selected from the group consisting of hydrocarbons and esters at a temperature in the range of about 10° to about 50° thereby having the perfume impregnated and absorbed into the granulated copolymer.

DETAILED DESCRIPTION OF THE INVENTION

The ethylene-vinyl acetate copolymer used in the present invention has a vinyl acetate content in the range of 19% to 40%, preferably 25% to 33%, by weight. If the vinyl acetate content is lower than this range, a substantial absorption of perfume cannot be expected, and if it exceeds this range, the resulting product will swell and soften remarkably.

It is necessary that the ethylene-vinyl acetate copolymer used in the invention be preformed into granules preferably having a spherical, cylindrical or like shape of a diameter of about 1 to about 10 mm, particularly about 2 to about 6 mm, although the shape of the granules is not limited thereto.

The perfume used in the present invention contains as an essential component hydrocarbons and/or esters. As hydrocarbons there may be exemplified monoterpene hydrocarbons such as limonene, α-pinene and β-pinene, sesquiterpene hydrocarbons such as caryophyllene, santalene, thujopsene and cedrene, diterpene hydrocarbons such as abietin and camphorene, and aromatic hydrocarbons such as p-cymene and styrene. As esters there may be exemplified aliphatic and aromatic carboxylic acid esters having usually not more than 20, preferably not more than 15, carbon atoms, such as isoamyl acetate, geranyl acetate, citronellyl acetate, linalyl acetate, benzyl acetate, benzyl benzoate, benzyl salicylate, cinnamyl cinnamate, isoamyl undecylate and cedryl acetate.

The perfume used in the invention is usually a mixed perfume and it is desirable that not less than 30%, particularly not less than 50%, of all the perfume components be occupied by the hydrocarbons and/or esters as exemplified above. The perfume may contain a fixative. As the fixative it is also preferable to use hydrocarbon and ester type fixatives.

If hydrocarbons or esters are little contained as a perfume component, a sufficient effect of impregnation of the perfume cannot be expected.

The operation for impregnation and absorption of the perfume is carried out by mixing the perfume and the granulated copolymer at a temperature in the range of about 10° C. to about 50° C. Operating temperatures higher than 50° C. would cause a change in quality of the perfume or other bad influence, and if the operating temperature is too low, it will be impossible to obtain a sufficient effect of absorption of the perfume.

In the mixing of the perfume and the granulated copolymer, it is desirable that the perfume be used in an equivalent amount, preferably in an amount ranging from about 5% to about 50% by weight, based on the amount of the granulated copolymer, and that substantially all the perfume present in the system be impregnated and absorbed into the granulated copolymer.

The granulated ethylene-vinyl acetate copolymer containing the perfume thus obtained may increase in its volume according to the amount of the perfume impregnated and absorbed therein, but it will never exhibit a marked softening, deformation, collapse or the like. Besides, because the perfume content is high as previously noted, it is sufficient to use only a very small amount of such perfume-impregnated granules in the case of using the granules as a volatilization matrix, and the granules can be put to the use of aromatics and like commodities by merely charging or sealing into a simple and light container such as, for example, a bag made of a non-woven fabric or a pack of polyethylene film having a vent hole.

In this molded article, moreover, the perfume is impregnated and absorbed therein in the form of a plasticizer for resin or the like, so that its volatilization is slow and durable, and as to its effective volatilization percentage, it is possible to attain a very high value of not less than 50%.

Furthermore, the molded article can be colored beautifully simultaneously with the impregnation and absorption of the perfume easily by dissolving an oil-soluble coloring matter of a desired color beforehand in the perfume.

The following are working examples of the present invention, but it is to be understood that the vinyl acetate content of the granular ethylene-vinyl acetate copolymers used therein and the shape, etc. of the resultant molded articles are not limited to those exemplified therein.

EXAMPLE 1

70 g. of transparent pellets (each being a spherical body having a diameter of about 5 mm) of an ethylene-vinyl acetate copolymer "EVAFLEX-150" (manufactured by Mitsui Polychemical Co., vinyl acetate content 33%) and 30 g. of a mixed lemon perfume (containing 32 wt.% of limonene and other hydrocarbons) which had been yellowed with Oil yellow 3G were sealed into an eggplant type flask (capacity: 2 liters) of a rotary evaporator and the flask was rotated at a rate of 40 r.p.m. In about 20 minutes the pellets absorbed the perfume nearly completely. In this stage the surfaces of the pellets were wet, so the rotation was further continued; as a result the perfume penetrated into the pellets, thus allowing the surfaces of the pellets to dry gradually, and after 1 hour there were obtained perfume-containing pellets having a good fluidity. The pellets were dry, translucent and yellow.

10 g. of the perfume-containing pellets were charged into a bag made of a thin non-woven fabric and the bag thus charged with the pellets was allowed to stand for 50 days within a flush toilet (3.8 m$^3$). The performance of the pellets as an aromatic was evaluated by an organoleptic panel test; as a result, the fragrance intensity during that period proved to be in the range of 4 to 2.75 (according to the 6-stage odor indication method).

After termination of the above period, the volatilization percentage of the perfume was determined. As a result, it proved to be 58% (loss of weight 1.74 g./amount of perfume impregnated 3 g. × 100) and thus a very good result could be obtained.

EXAMPLE 2

70 g. of transparent pellets (each being a spherical body having a diameter of about 5 mm) of an ethylene-vinyl acetate copolymer "EVAFLEX-460" (manufactured by Mitsui Polychemical Co., vinyl acetate content 19%) and 30 g. of a mixed lemon perfume (containing 32 wt.% of limonene and other hydrocarbons) which had been yellowed with Oil yellow 3G were sealed into the flask of the rotary evaporator in the same way as in Example 1 and the flask was rotated at a rate of 30 r.p.m. while dipping the lower surface of the flask in a water bath held at 45° C. After 5 hours, there were obtained perfume-impregnated pellets like the pellets obtained in Example 1. The performance of the pellets as an aromatic was just the same as that evaluated in Example 1.

EXAMPLE 3

70 g. of transparent pellets of the "EVAFLEX-150" described in Example 1 and 30 g. of a mixed fragrant olive perfume (containing 43% of esters such as ethyl acetate, amyl acetate, amyl butyrate, ethyl caproate and benzyl acetate) which had been colored to orange color were sealed into the flask of the rotary evaporator in the same way as in Example 1 and the flask was rotated at a rate of 30 r.p.m. while dipping the lower surface of the flask in a water bath held at 30° C. After 2 hours, there were obtained perfume-impregnated pellets like the pellets obtained in Example 1. The performance of the pellets as an aromatic was just the same as that evaluated in Example 1.

What is claimed is:

1. A slowly releasing perfume composition prepared by mixing a granulated ethylene-vinyl acetate copolymer having a vinyl acetate content in the range of 19 to 40% by weight and a perfume, said perfume containing as an essential component at least one fragrant component selected from the group consisting of hydrocarbons and esters the total amount of said hydrocarbons and esters in said perfume being not less than about 30%, at a temperature in the range of about 10° C. to about 50° C. to thereby allow said perfume to be absorbed in said granulated copolymer and wherein the diameter of each granule of said granulated copolymer is in the range of about 1 to about 10 mm.

2. The composition of claim 1 wherein said hydrocarbons are monoterpene hydrocarbons, sesquiterpene hydrocarbons, diterpene hydrocarbons and aromatic hydrocarbons.

3. The composition of claim 1 wherein said esters are aliphatic and aromatic carboxylic acid esters having not more than 20 carbon atoms.

4. The composition of claim 1 wherein said perfume is used in an equivalent amount or less based on the amount of said granulated copolymer and substantially all the amount thereof is absorbed in said granulated copolymer.

* * * * *